(12) United States Patent
Cotton

(10) Patent No.: US 6,626,982 B1
(45) Date of Patent: Sep. 30, 2003

(54) COMPOUND STORAGE

(75) Inventor: Ronald Cotton, Macclesfield (GB)

(73) Assignee: AstraZeneca AB (SE)

( * ) Notice: Subject to any disclaimer, the term of this patent is extended or adjusted under 35 U.S.C. 154(b) by 0 days.

(21) Appl. No.: 09/743,918

(22) PCT Filed: Jul. 22, 1999

(86) PCT No.: PCT/GB99/02386

§ 371 (c)(1),
(2), (4) Date: Jan. 17, 2001

(87) PCT Pub. No.: WO00/06297

PCT Pub. Date: Feb. 10, 2000

(30) Foreign Application Priority Data

Jul. 28, 1998 (GB) ................................................ 9816316

(51) Int. Cl.$^7$ ................................................ B01D 53/02
(52) U.S. Cl. ........................................ 95/148; 96/143
(58) Field of Search ............................ 95/148, 90, 116, 95/141, 108, 143

(56) References Cited

U.S. PATENT DOCUMENTS

| | | | | |
|---|---|---|---|---|
| 4,003,257 A | * | 1/1977 | Fletcher et al. | ................ 422/89 |
| 4,062,652 A | | 12/1977 | Rolfo-Fontana | |
| 4,744,221 A | * | 5/1988 | Knollmueller | ............... 62/46.1 |
| 5,704,965 A | | 1/1998 | Tom et al. | |
| 5,751,629 A | | 5/1998 | Nova et al. | |

FOREIGN PATENT DOCUMENTS

| | | |
|---|---|---|
| EP | 0 182 612 | 5/1986 |
| EP | 0 915 329 | 5/1999 |

* cited by examiner

Primary Examiner—Robert A. Hopkins
(74) Attorney, Agent, or Firm—Fish & Richardson PC

(57) ABSTRACT

The invention relates to adsorbing chemical samples onto inert carriers to form highly stable free flowing solid for long term storage in, for example, a proprietary compound collection.

15 Claims, 3 Drawing Sheets

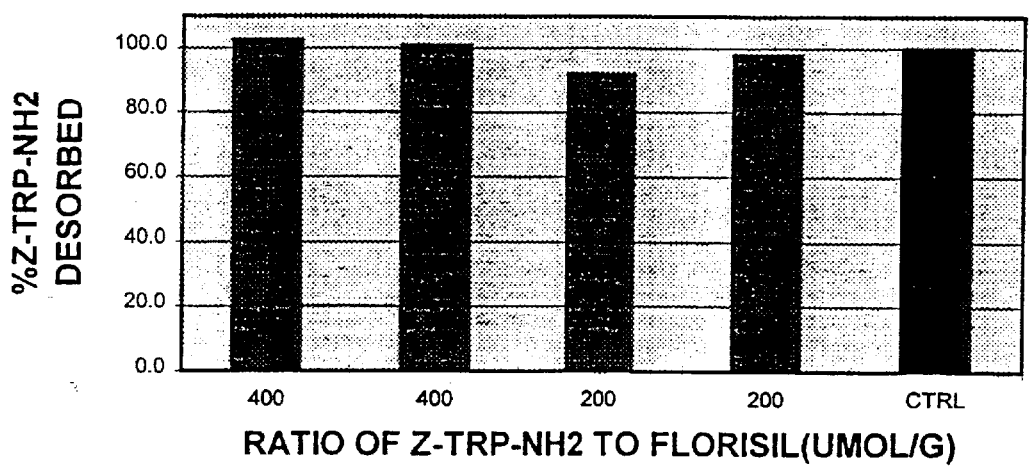

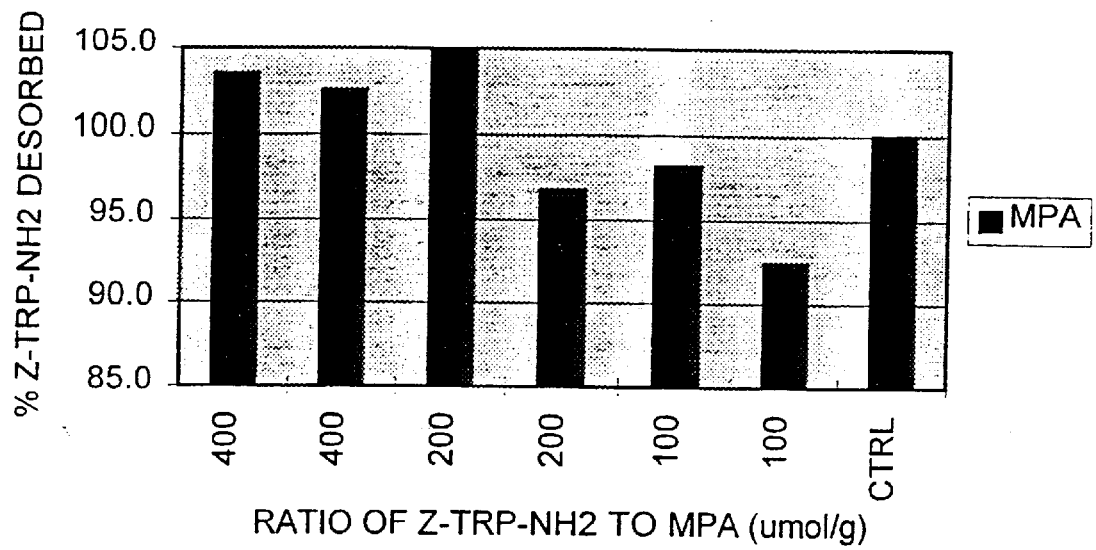

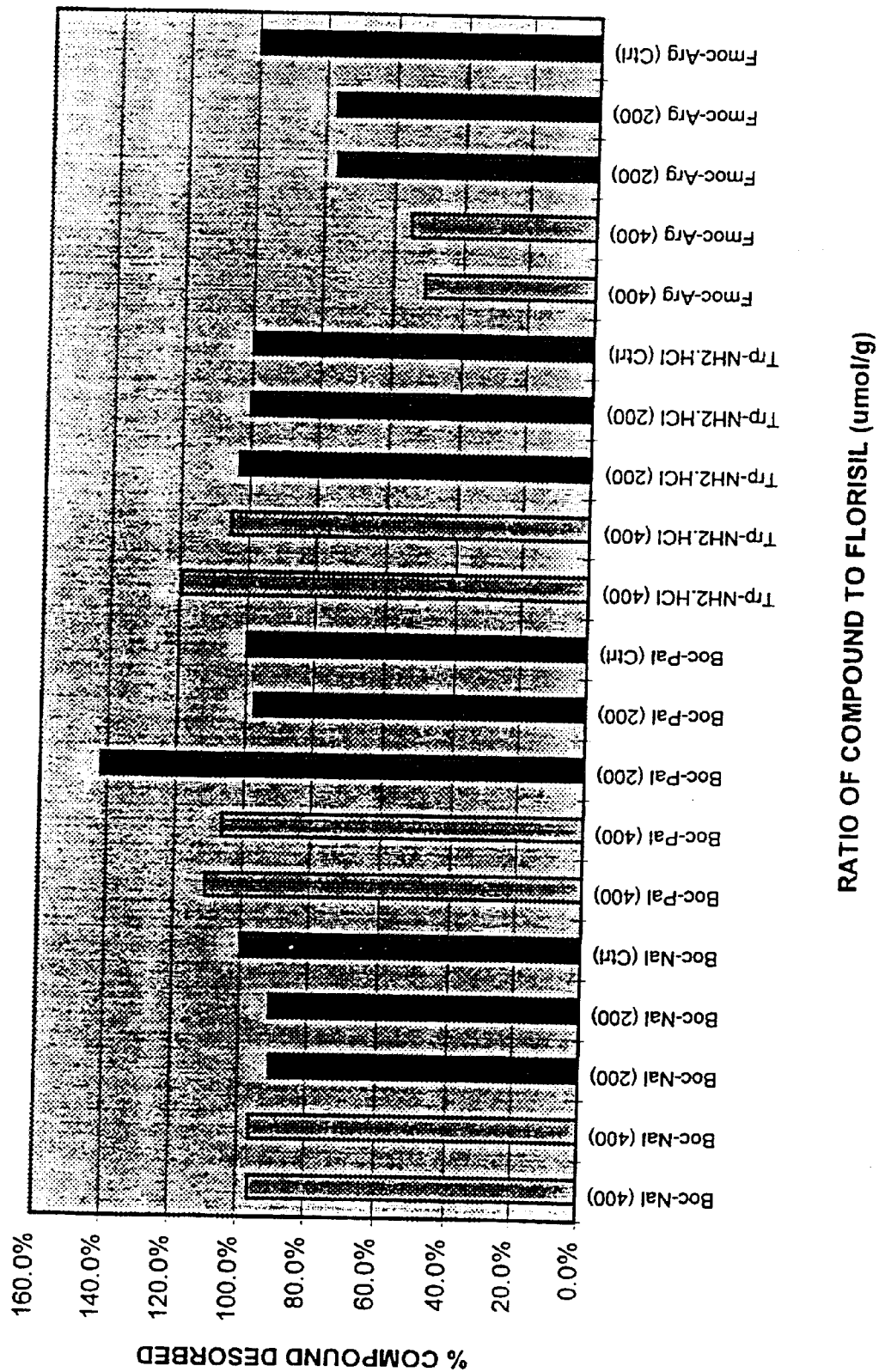

COMPOUND STORAGE

This application is the national phase of international application PCT/GB99/02386 filed Jul. 22, 1999 which designated the U.S.

The invention relates to adsorbing chemical samples onto inert carriers to form highly stable free flowing solid for long term storage in, for example, a proprietary compound collection.

Large collections of chemical compounds are valuable assets of research organisations. Compound collections are used in the search for agents with novel pharmaceutical, agrochemical or other fine chemical applications and are a valuable source of structural and chemical diversity used in identifying new leads as potential inhibitors of a biological target. Compound collections may contain more than 100,000 different compounds and due to increasingly efficient compound acquisition, either through commercial sources, or by high throughput synthesis, compound collections with more than 1 million different compounds are now of a typical size in some research organisations.

The handling of samples within large compound collections for the purposes of storage, retrieval and testing presents numerous problems. In most organisations samples are obtained and stored as crystalline or amorphous powders and can be dispensed relatively easily by weighing, although this often needs to be done manually because of the varying nature of the solids. Some samples are made or obtained as glassy solids, syrups, oils or liquids and are subsequently stored in these forms. The weighing of these samples is often very time consuming and wasteful.

High throughput multiple parallel synthesis (HTMPS) can generate very large numbers of individual compounds, typically 100–5000 per week, but the sample size is usually small, <100 mg. To try and obtain all or most of these samples as crystalline or amorphous powders using the methods normally available to chemists would increase the overall synthesis time to such an extent that the HTMPS process would be impractical. To avoid this problem, compounds from HTMPS are stored sometimes as dry films or as solutions, usually in dimethyl sulphoxide (DMSO). The dispensing of compounds stored as dry films is often very difficult, and the difficulty increases significantly as the sample size decreases. Compounds stored as solutions can be dispensed quickly and accurately, but the manipulation and storage of the solutions subsequent to, and after, dispensing can be very problematical especially in compound handling systems designed to handle solids. In addition, some samples are unstable in solution and decompose on prolonged storage, even at low temperatures.

Increasingly the demands of a compound collection are changing. With the advent of high throughput screening (HTS) a whole compound collection of, for example, 100,000 compounds may be screened in a number of days against a new biological target, using automated or semi-automated procedures. Faced with the need for more rapid dispensing of compounds from the compound collection, the small sample size needed and the large numbers of different sample types existing in a compound collection, current systems of storage and dispensing are increasingly incompatible with modem needs. For example, a typical sample size of compound sample needed to be dispensed for HTS may be less than 0.1 mg, but despite weight variations of ±10% being tolerated for the purposes of screening, including HTS, it is not practicable to rapidly dispense such small sample sizes.

We have found that it is possible to store and retrieve compound samples, even after an extended duration of storage, by adsorbing the compound onto an inert carrier.

We have found that if the same inert carrier is used for a number of compounds, of different molecular weight, then only a single weight or volume of compound adsorbed onto an inert carrier is required to produce a substantially similar quantity (up to +/−15%, ideally +/−10%), in moles, of compound sample, after being extracted from the inert carrier, provided that the amount of inert carrier is in a large excess to the compound sample adsorbed onto it. Such a system lends itself to automation and hence rapid dispensing of compound samples because similar/identical weights, or volumes, of inert support with adsorbed compound can be measured in order that a similar amount, in moles, of compound sample is dispensed, after extraction, even when the concentration of compound adsorbed onto the inert support varies from sample to sample.

We present as a first feature of the invention a method of dispensing a compound sample, which comprises (1) measuring an amount of compound which is adsorbed onto an inert carrier, (2) extracting the compound from the inert carrier, and (3) dispensing the compound sample.

Preferably the inert carrier is in a large excess to the compound adsorbed onto it. The molar amount of the compound extracted from the inert carrier when in large excess to the compound adsorbed onto it, is directly related to the amount of compound plus inert carrier measured and not the molecular weight of the compound.

A further feature of the invention is an inert carrier having adsorbed onto it a compound characterised in that the compound is adsorbed onto a large excess of the inert carrier.

A further feature of the invention is a method of dispensing compound samples of substantially similar molar quantity which comprises (1) for each compound measuring an amount of compound which is adsorbed onto a large excess of an inert carrier, wherein the amount measured is substantially the same for each sample (2) extracting the compounds from the inert carrier, and (3) dipensing the compound samples.

The exact ratio of inert carrier to adsorbed compounds is unimportant provided that there is a "large excess" of inert carrier, for guidance it is intended that there is at least a 100, preferably at least a 200, 500, 1000 or 5,000, fold excess of inert carrier, in grams, compared with adsorbed compound, in moles. Preferred levels of adsorption are less that 400 µmol, preferably less than 300 µmol or less than 200 µmol, of adsorbed compound per gram of inert carrier.

The measurement used in dispensing the inert carrier plus adsorbed compound may be by weight, volume or any other means, preferably by volume. Typical weights that may be measured with levels of adsorption described above include from 10 to 250 mg, preferably 10 to 125 mg, of inert support and adsorbed compound. Typical volumes that may be measured include from 15 µl to 600 µl, preferably from 15 µl to 300 µl, depending upon the density of the inert carrier used.

We present as a further feature of the invention a method of dispensing a subgram (preferably less than 1 mg, or less than 0.1 mg, or even less than 0.05 mg) amount of compound sample, which comprises (1) adsorbing the compound onto an inert carrier, wherein the inert carrier is in a large excess to the compound, (2) measuring an amount of the adsorbed compound and inert carrier, (3) extracting the compound from the inert carrier and (4) dispensing the compound sample.

Ideally adsorption is achieved by contacting a solution of the compound dissolved in a suitable solvent, with the inert carrier and then removing the solvent, for example by evaporation. Ideally extraction is achieved by contacting the inert carrier with the required compound adsorbed on it with a suitable solvent for the adsorbed compound, which is not a solvent for the inert carrier, and separating the inert carrier from the solution.

The compound may be one of any number of different compounds, such as within a compound collection and as such represents a further feature of the invention.

Suitable inert carriers include those made from silicon, either as silicon oxides, such as sands, glass etc.; or in the form of silicates, such as mica, clay, feldspar, including, for example, the following commercially available silicas; Florosil™, Davisil™, Kiesegel™, C18 derivatised silica (C18), silanised silca gel 60 (Si-60) and other bonded silicas. Other inert carriers include aluminas, charcoals, resins, polymers and celluloses. Particular materials are microporous glass, controlled pore glass, or silicates (such as magnesium silicate or derivatised silica such as those listed above). Preferably the material is a silicate or bonded silicate such as magnesium silicate, Florosil™, Davisil™, Kiesegel™, C18 and Si-60, in particular the preferred inert carrier is Florisil™.

Florosil™ may be obtained from Merck KGaA. Davisil™ may be obtained from Aldrich. Octadecyl-functionalized silica gel may be obtained from Aldrich. Silica gel 60 silanised may be obtained from Merck KGaA.

Preferably the inert carrier is conditioned or treated in a way to provide an even particle size (preferably the particle size is from 5 to 200 microns and of low particle size distribution) for ease of flowing and even adsorption. Preferably the inert carrier has a porous surface (preferably greater than 3 $m^2/g$ and ideally greater than 200 $m^2/g$), to maximise the amount of compound adsorbed.

Presented as a further feature of the invention is a method for storing and dispensing a number of different compounds with different physical properties which comprises (1) adsorbing each compound onto an inert support, (2) storing the adsorbed compound until the compound is required, (3) extracting the compound from the carrier and (4) dispensing the compound.

Presented as a further feature of the invention is a method of storing a number of different compounds in a compound collection for an extended duration whilst providing for significant recovery of the compound after storage which comprises adsorption of each compound onto an inert carrier, preferable a silicon oxide or silicate carrier.

A further feature of the invention is a compound collection comprising a number of different compounds wherein each compound has been adsorbed onto an inert carrier, preferably a silicon oxide or silicate carrier, and preferably where each compound is adsorbed onto a large excess of inert carrier.

The inert carrier may be separated from the solvent by using either manual techniques, such as by filtration, which represent an addition step, or preferably and simply by using an inert carrier which is of a higher density than the solvent such that the inert carrier sinks to the bottom of the vessel and the compound sample dissolves in the solvent top layer. Alternatively the inert carrier may have a lower density than the solvent and rise to the surface of the vessel and the compound sample dissolves in the solvent bottom layer. When utilising a system of separation where the inert solvent rises or falls in the solvent it is preferable to use an inert carrier that does not swell in the solvent so that the solvent layer is not reduced in depth. The dissolved sample may then be retrieved by skimming the top layer or draining the bottom layer, as appropriate, or by dipping the tip of a pipette into the solvent layer for direct separation and dispensing.

By use of the term "extended duration" we mean that we have found that "significant recovery" (which means >50% w/w, ideally >80% w/w, preferably >90% w/w recovery of the sample) of compound may be extracted from the inert carrier even after a period of storage at room temperature of at least 6 months, and in particular over a period of more than 1 year.

The "number" of compounds in a compound collection which may be stored by the techniques as described above is not limited by the invention, ideally the invention may be used for storage of compounds in compound collections where the number of different compounds stored may be more than 5, 50, 100, $10^3$, $10^4$ or even more than $10^6$. The invention may also be applied to a subset of a compound collection.

By the use of the term "compounds" we refer to compounds which are able to be adsorbed onto inert carriers. The physical and chemical properties of the compounds are generally unimportant in applying the present invention. However, it will be appreciated that this method is not suited to compounds with low boiling points. Preferred compounds are those stored in compound collections of pharmaceutical, biotechnology or agrochemical companies. Preferred compounds are organic molecules of molecular weight of less than 2000 Daltons, and ideally of 1000 Daltons or less.

The inert carrier adsorbed with a compound provides a powder with very similar physical properties even when compounds are adsorbed which have different physical properties. The handling of samples from collections containing large numbers of compounds is greatly facilitated as all compounds can be stored as free flowing, easily measured, uniform powders. Further advantages include:

Amount of compound adsorbed on inert carrier up to 1 mmol per gram,

Carrier+compound give a free flowing powder;

Even distribution of compound on inert carrier;

Compound can be quantitatively and reproducibly adsorbed and extracted from inert carrier;

Storage and dispensing of compounds which exist normally as liquids, gums or glasses;

Adsorption onto an inert carrier produces solid powders with very similar handling characteristics;

For the reasons outlined above, robotic handling and weighing of samples is much simpler than for non-adsorbed materials, thereby enabling rapid dispensing of large numbers of compounds; and Compounds for which only small samples are available can be dispensed far more economically.

FIG. 1. shows the amount of Z-Trp-$NH_2$ extracted by using DMSO from a given amount of Florisil™ bearing adsorbed Z-Trp-$NH_2$.

FIG. 2. shows the amount of Z-Trp-$NH_2$ extracted by DMSO from a given amount of Micropil-A™ (MPA) bearing adsorbed Z-Trp-$NH_2$.

FIG. 3. shows for a variety of different compounds the amounts extracted by DMSO of Florisil™ bearing the adsorbed compounds.

EXAMPLE 1

The following procedure was used to check the adsorption/desorption of a test compound, Z-Trp-$NH_2$.

1. 16.9 mg (50 $\mu$mol) of Z-Trp-$NH_2$ in DMSO (0.5–5 ml) added to carrier (100 mg, 225 mg and 475 mg).
2. Mix briefly.
3. Evaporate off DMSO using centrifugal evaporator (70°/1 hr).

4. Mix resulting solid with spatula to ensure distribution as even as possible.
5. Weigh duplicate samples (to contain nominal 10 μmol Z-Trp-NH$_2$) into vials.
6. Add DMSO to achieve 10$^{-2}$M conc. (nominal).
7. Dilute for HPLC analysis and compare with 10$^{-2}$M control solution of Z-Trp-NH$_2$ similarly diluted.

TABLE 1

| Carrier | Physical Properties and appearance before compound adsorption |
|---|---|
| Micropil A ™ (MPA), microporous glass | 7–20 μm beads, pore diameter 300 ηM, surface area 100–150 m$^2$/g. Homogeneous, free-flowing powder. No swelling in DMSO |
| Florisil ™, magnesium silicate | 150–250 μm irregular particles, surface area 300 m$^2$/g. Homogeneous free-flowing powder. No swelling in DMSO |
| C18 derivatised silica | Particle size <50 μm. Homogeneous free-flowing powder. No swelling in DMSO |
| Davisil ™ | 60–100 mesh irregular particles, pore diameter 600 ηM, surface area 480 m$^2$/g. Homogeneous free flowing powder. No swelling in DMSO |
| Silanised Silica gel 60 (Si60) | 63–200 μm irregular particles, pore diameter 600 ηM, surface area 500 m$^2$/g. Homogeneous free flowing powder. No swelling in DMSO |

The physical appearances of the carriers with adsorbed Z-Trp-NH$_2$, Boc-Pal, Boc-Nal, Trp-NH$_2$ and Fmoc-Arg are described in Table 2.

TABLE 2

| Carrier | Compound Loading μmol/g | Comment |
|---|---|---|
| MPA | 400$^a$ | Free flowing, homogeneous powder |
| MPA | 200$^a$ | Free flowing, homogeneous powder |
| MPA | 100$^a$ | Free flowing, homogeneous powder |
| Florisil ™ | 400$^b$ | Free flowing, homogeneous powder |
| Florisil ™ | 200$^b$ | Free flowing, homogeneous powder |
| C18 Silica | 400$^c$ | Free flowing, homogeneous powder |
| C18 Silica | 200$^c$ | Free flowing, homogeneous powder |
| Davisil ™ | 400$^d$ | Free flowing, homogeneous powder |
| Davisil ™ | 200$^d$ | Free flowing, homogeneous powder |
| Si 60 | 400$^d$ | Free flowing, homogeneous powder |
| Si 60 | 200$^d$ | Free flowing, homogeneous powder |

$^a$Compound tested = Z-Trp-NH$_2$
$^b$Compound tested = Z-Trp-NH$_2$, Boc-Nal, Boc-Pal, Trp-NH$_2$.HCl, Fmoc-Arg
$^c$Compound tested = Boc-Nal, Boc-Pal, Trp-NH$_2$.HCl, Fmoc-Arg
$^d$Compound tested = Z-Trp-NH$_2$, Boc-Nal, Boc-Pal, Trp-NH$_2$.HCl

EXAMPLE 2

Adsorption of ZTrp-NH$_2$ onto Florisil™ to Give Approximate Loadings of 200 and 400 μmol/g Z-Trp-NH$_2$ (169 mg) was dissolved in DMSO (50 ml) to give a 10 mM solution. Aliquots of the solution (5 ml, 50 μmol) were added to a 100 mg and a 225 mg sample of Florisil™ in 2-dram glass vials. The samples were vortexed for approximately one minute and the DMSO removed in vacuo by evaporation at 70° for 1 h in a centrifugal evaporator (GeneVac Atlas HT4™). After evaporation the samples were removed and checked visually. In each case dry solids were obtained in the form of free flowing powders virtually indistinguishable from the original Florisil™. The nominal loadings of the adsorbed samples were calculated as 207 and 427 μmol/g of Z-Trp-NH$_2$.

Desorption of Z-Trp-NH$_2$ From ZTrp-NH$_2$/Florisil™ Samples

Duplicate amounts (11.7 and 24.2 mg respectively) of the 427 and 207 μmol/g Z-Trp-NH$_2$/Florisil™ samples were weighed into glass vials. DMSO (0.5 ml) was added to each vial and the vials were agitated gently for 15 min to give a nominal concentration of 10 mM of Z-Trp-NH$_2$. Aliquots from each vial were diluted 100-fold with CH$_3$CN and analysed by RP-HPLC monitoring by UV at 230 ηM. The peak areas obtained for the desorbed Z-Trp-NH$_2$ DMSO solutions were compared with those obtained using a 10 mM control soln of Z-Trp-NH$_2$ in DMSO similarly diluted. The results are given in table 3

TABLE 3

| Ratio of Z-Trp-NH$_2$ to Florisil ™ (μmol/g) | Conc. (mM) of Z-Trp-NH$_2$ in DMSO after desorption from Florisil |
|---|---|
| 400 | 10.26 |
| 400 | 10.09 |
| 200 | 9.21 |
| 200 | 9.79 |
| Control | 10.00 |

EXAMPLE 3

Further Absorption/Desorption Experiments with Florisil™.

The following compounds with a range of physical/chemical properties were selected.

| Compound | Comment |
|---|---|
| Boc-Naphthylalanine (Boc-Nal) | Lipophilic carboxylic acid |
| Boc-Pyridylalanine (Boc-Pal) | Weakly basic pyridine and carboxylic acid |
| Tryptophan amide hydrochloride (Trp-NH$_2$.HCl) | Amine hydrochloride salt |
| Fmoc-Arginine (Fmoc-Arg) | Zwitterion - strongly basic guanidine + carboxylic acid |

Using a procedure analogous to that used for Z-Trp-NH$_2$ the following results were obtained (Table 4 and FIG. 3)

TABLE 4

| Compound | Ratio of Compound to Florisil ™ (μmol/g) | Conc. (mM) of Compound in DMSO after desorption from Florisil ™ |
|---|---|---|
| Boc-Nal | 397.5 | 9.64 |
| Boc-Nal | 400.6 | 9.64 |
| Boc-Nal | 200.1 | 9.06 |
| Boc-Nal | 200.0 | 9.10 |
| Boc-Nal (control) | | 10.00 |
| Boc-Pal | 397.5 | 11.06 |
| Boc-Pal | 400.6 | 10.63 |
| Boc-Pal | 200.1 | 14.20 |
| Boc-Pal | 200.0 | 9.75 |
| Boc-Pal (control) | | 10.00 |
| Trp-NH2.HCl | 397.5 | 11.93 |
| Trp-NH2.HCl | 400.6 | 10.51 |
| Trp-NH2.HCl | 200.1 | 10.31 |
| Trp-NH2.HCl | 200.0 | 10.04 |
| Trp-NH2.HCl (control) | | 10.00 |
| Fmoc-Arg | 397.5 | 5.11 |
| Fmoc-Arg | 400.6 | 5.53 |

TABLE 4-continued

| Compound | Ratio of Compound to Florisil™ (μmol/g) | Conc. (mM) of Compound in DMSO after desorption from Florisil™ |
|---|---|---|
| Fmoc-Arg | 200.1 | 7.65 |
| Fmoc-Arg | 200.0 | 7.70 |
| Fmoc-Arg (control) | | 10.00 |

Three of the four compounds gave satisfactory results, comparable to those obtained with Z-Trp-NH$_2$. The apparent low release of Fmoc-Arg is due to the fact that this compound decomposes in DMSO. In a control experiment with Fmoc-Arg, in which no Florisil™ was added, it was not possible to detect any Fmoc-Arg by HPLC after centrifugal evaporation and dissolution into DMSO. Similarly, Fmoc-Arg at $10^{-2}$ M in DMSO decomposes completely after 24 hours at ambient temperature In contrast, Fmoc-Arg is stable when adsorbed onto Florisil™ although some decomposition occurs during the adsorption/desorption process when DMSO is present.

What is claimed is:

1. A compound collection comprising a number of different compounds wherein each compound has been adsorbed onto an individual inert carrier.

2. A compound collection as claimed in claim 1 in which the compound is adsorbed onto a large excess of the inert carrier.

3. A compound collection as claimed in claim 1 wherein inert carrier is at least 100 fold in excess, when measured in grams, compared to the amount of compound, when measured in moles.

4. A compound collection as claimed in either claim 1, 2, or 3 wherein the inert carrier is a silicate or bonded silicate.

5. A compound collection as claimed in claim 3 wherein the inert carrier is a silicate or bonded silicate that is magnesium silicate, silica gel, C18 derivatised silica or SI-60 silanised silica gel.

6. A method of dispensing a compound sample from a compound collection, wherein each compound has been adsorbed onto an individual inert carrier, which comprises (1) measuring an amount of material having compound which is adsorbed onto an inert carrier, (2) extracting the compound from the inert carrier, and (3) dispensing the compound sample.

7. A method as claimed in claim 6 wherein the inert carrier is in a large excess to the compound adsorbed on it.

8. A method of dispensing selected compounds of substantially similar molar quantity from a compound collection, which comprises (1) for each selected compound measuring an amount of compound which is adsorbed onto a large excess of an individual inert carrier, wherein the amount measured is substantially the same for each sample (2) extracting the selected compounds from the inert carrier, and (3) dispensing the selected compound.

9. A method of dispensing a subgram amount of a selected compound from a compound collection, which comprises (1) adsorbing the selected compound onto an individual inert carrier, wherein the inert carrier is in a large excess to the compound, (2) measuring out a sample of the selected adsorbed compound and inert carrier, (3) extracting the selected compound from the inert carrier and (4) dispensing the selected compound.

10. A method for storing and dispensing a number of different compounds with different physical properties which comprises (1) adsorbing each compound onto an individual inert support, (2) storing the adsorbed compound until the compound is required, (3) extracting the compound from the carrier and (4) dispensing the compound.

11. A method as claimed in claim 8, 9, or 10 wherein extraction of the compound from the inert carrier is achieved by contacting the adsorbed compound and inert carrier with a solvent for the adsorbed compound, which is not a solvent for the inert carrier, and separating the inert carrier from the solution.

12. A method of storing a number of different compounds for an extended duration whilst providing for significant recovery of the compound after storage which comprises adsorption of each compound onto an individual inert carrier.

13. A method as claimed in claim 8, 9, 10 or 12 wherein adsorption is achieved by contacting a solution of the compound dissolved in a suitable solvent with the inert carrier and removing the solvent.

14. A method as claimed in claim 10 wherein extraction of the compound from the inert carrier is achieved by contacting the adsorbed compound and inert carrier with a solvent for the adsorbed compound, which is not a solvent for the inert carrier, and separating the inert carrier from the solution.

15. A method as claimed in claim 10 or 12 wherein adsorption is achieved by contacting a solution of the compound dissolved in a suitable solvent with the inert carrier and removing the solvent.

* * * * *